United States Patent
Glaser et al.

(10) Patent No.: US 12,329,658 B2
(45) Date of Patent: Jun. 17, 2025

(54) GRAFT DELIVERY DEVICE WITH ACCURATE DISPENSING

(71) Applicant: Warsaw Orthopedic, Inc., Warsaw, IN (US)

(72) Inventors: Adam D. Glaser, Germantown, TN (US); Andrea L. Hartman, Memphis, TN (US); Jeffrey L. Gum, Peewee Valley, KY (US); Ronald A. Lehman, Jr., Tenafly, NJ (US); Christopher R. Good, Great Falls, VA (US); Douglas John Fox, Jr., Phoenix, AZ (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 506 days.

(21) Appl. No.: 17/670,930

(22) Filed: Feb. 14, 2022

(65) Prior Publication Data

US 2023/0255789 A1 Aug. 17, 2023

(51) Int. Cl.
*A61B 17/88* (2006.01)
*A61F 2/46* (2006.01)
*A61B 17/00* (2006.01)

(52) U.S. Cl.
CPC ........ *A61F 2/4601* (2013.01); *A61B 17/8825* (2013.01); *A61B 17/8827* (2013.01); *A61B 2017/00407* (2013.01); *A61F 2002/4632* (2013.01); *A61F 2002/4663* (2013.01)

(58) Field of Classification Search
CPC ........................... A61F 2/4601; A61B 17/8827
See application file for complete search history.

(56) References Cited

U.S. PATENT DOCUMENTS

| | | | | |
|---|---|---|---|---|
| 2,735,431 | A | * | 2/1956 | Swanson ........... A61M 5/31595 604/223 |
| 4,338,925 | A | * | 7/1982 | Miller ................ A61B 17/8811 604/61 |
| 4,583,974 | A | * | 4/1986 | Kokernak ......... A61M 5/31586 604/920 |
| 10,687,879 | B2 | | 6/2020 | Dewey et al. |
| 10,687,880 | B2 | | 6/2020 | Deridder et al. |
| 11,969,194 | B2 | * | 4/2024 | Reves ................ A61B 17/8811 |

(Continued)

OTHER PUBLICATIONS

International Search Report and Written Opinion in Application No. PCT/IB2023/050850 dated May 8, 2023.

*Primary Examiner* — Nicholas W Woodall
(74) *Attorney, Agent, or Firm* — FOX ROTHSCHILD LLP (57) ABSTRACT

Disclosed herein are systems and methods for graft delivery with accurate dispensing. For example, a device for delivering graft material to a target site includes an actuation mechanism and a tube. The tube defines a lumen and an open end and is configured to receive graft material through the open end. The tube includes a pressure relief opening and a dosage window. The pressure relief opening is disposed in a wall of the tube, defining a pressure chamber between the open end and the pressure relief opening. The device further includes a plunger positioned within the lumen of the tube and coupled to the actuation mechanism such that at least a portion of the plunger (or the actuation mechanism) is visible through the dosage window. The actuation mechanism is configured to advance the plunger toward the open end to deliver graft material through the open end.

14 Claims, 6 Drawing Sheets

(56) References Cited

U.S. PATENT DOCUMENTS

| | | | |
|---|---|---|---|
| 2007/0217282 A1* | 9/2007 | Lidgren | B01F 33/50112 |
| | | | 366/195 |
| 2014/0257232 A1 | 9/2014 | Mathur et al. | |
| 2014/0257313 A1 | 9/2014 | Frey et al. | |
| 2017/0304077 A1 | 10/2017 | Shadeck et al. | |
| 2018/0125558 A1* | 5/2018 | Flores | A61B 17/8833 |
| 2019/0314040 A1 | 10/2019 | Greenhalgh et al. | |
| 2023/0210540 A1* | 7/2023 | Martineau | A61B 17/12186 |
| | | | 604/508 |

* cited by examiner

GRAFT DELIVERY DEVICE WITH ACCURATE DISPENSING

FIELD

The present technology is generally related to systems and methods for dispensing bone graft material during a procedure.

BACKGROUND

Concepts presented herein relate to delivery of graft material to a target site, e.g., during a procedure. Bone graft is important in orthopedic procedures for the repair of bone defects caused by injury, disease, wounds, or surgery. Example applications that utilize graft material include rhinologic functional endoscopic sinus surgery (FESS), spinal, orthopedic and arthroscopic procedures. Conventionally, bone tissue regeneration is achieved by filling a bone defect with a bone material, for example, a bone graft. Graft material may include demineralized bone in a matrix or framework. Bone material can include bone from the patient's own body, synthetic bone material, natural substitute bone material or combinations thereof. Often times the bone material is mixed with liquid or a therapeutic agent, powder, fiber, or granular material. Graft material can be loose, or graft can be formed, e.g., into pellets or other configurations. Over time, the bone graft is incorporated by the host and new bone remodels the bone graft.

Regardless of the exact procedure, various instruments for delivery of graft material are currently employed to deliver the bone material to the bone defect. However, it can be difficult to dispense an accurate volume of graft material. This can lead to waste of time and/or effort and may lead to sub-optimal patient outcomes. Furthermore, transfer of bone material to the dispensing device is often done by crude, inaccurate, and/or messy packing of the bone dispensing device which can cause unwanted waste and spillage of bone material. It would therefore be desirable to provide a bone material dispensing device that allows easier loading of the bone material and is also able to deliver the bone material incrementally in controlled amounts to a bone defect.

This document describes methods and systems that are directed to addressing the problems described above, and/or other issues.

SUMMARY

The techniques of this disclosure generally relate to graft delivery with accurate dispensing.

In one aspect, the present disclosure provides a device for delivering graft material to a target site. The device includes an actuation mechanism and a tube defining a lumen and an open end. The tube is configured to receive graft material through the open end. The tube includes a dosage window and a pressure relief opening disposed in a wall of the tube, the pressure relief opening defining a pressure chamber between the open end and the pressure relief opening. The device further includes a plunger positioned within the lumen of the tube and coupled to the actuation mechanism such that at least a portion of the plunger or the actuation mechanism is visible through the dosage window. The actuation mechanism is configured to advance the plunger toward the open end to deliver graft material through the open end.

Implementations of the disclosure may include one or more of the following optional features. In some examples, the pressure relief opening is configured to allow fluid to escape the lumen as graft material is received through the open end into the pressure chamber. The portion of the plunger or the actuation mechanism that is visible through the dosage window may include a dose scale indicating an associated volume of graft material. The plunger may include a spring configured to provide a longitudinal force to the plunger in a direction away from the open end. In some examples, the volume of the lumen between the open end and the pressure relief opening is at least 2 cubic centimeters. The tube may be configured to engage with a guide sleeve of a robot arm. The tube may include one or more fiducial markings along its length, the one or more fiducial markings indicating a distance. The plunger may include a distal end which forms a seal with the lumen. In some examples, the distal end includes a series of ring grooves. The plunger may be formed of polyether ether ketone. In some examples, the actuation mechanism includes a ratchet mechanism. The tube may include a retention member disposed near the open end and configured to retain a graft loading device. In some examples, the graft loading device includes a graduated scale indicating a volume of graft material contained in the graft loading device and an actuator configured to transfer graft material from the graft loading device to the device and to compact the graft material in the pressure chamber.

In another aspect, the disclosure provides a method of delivering graft material to a target site. The method includes configuring a graft delivery device to receive graft material. The graft delivery device includes an actuation mechanism and a tube defining a lumen and an open end. The tube is configured to receive graft material through the open end. The tube includes a dosage window and a pressure relief opening disposed in a wall of the tube, the pressure relief opening defining a pressure chamber between the open end and the pressure relief opening. The device further includes a plunger positioned within the lumen of the tube and coupled to the actuation mechanism such that at least a portion of the plunger or the actuation mechanism is visible through the dosage window. The portion of the plunger or the actuation mechanism that is visible through the dosage window includes a dose scale. The actuation mechanism is configured to advance the plunger toward the open end to deliver graft material through the open end. And configuring the graft delivery device to receive graft material includes positioning the plunger in the lumen so that the pressure relief opening is exposed. The method further includes loading graft material into the pressure chamber of the graft delivery device, compacting the graft material to remove voids, positioning the open end of the tube of the graft delivery device at the target site, and actuating the actuation mechanism while observing the dose scale through the dosage window.

Implementations of the disclosure may include one or more of the following optional features. In some examples, configuring the graft delivery device to receive graft material includes positioning the plunger in the lumen so that a distal end of the plunger is adjacent to the pressure relief opening. Compacting the graft material may include compacting the graft material until graft material issues from the pressure relief opening. Loading graft material into the pressure chamber may include loading graft material using a graft loading device secured to a retention mechanism of the tube. Positioning the open end of the tube of the graft delivery device at the target site may include inserting a portion of the graft delivery device in a guide sleeve of a robotic system. The target site may be a facet of a vertebra or a location along a transverse process of a vertebra. In some examples, loading graft material into the pressure chamber of the graft delivery device includes attaching a graft loading device to the tube and transferring graft material from the graft loading device to the tube.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following terms shall have, for purposes of this application, the respective meanings set forth below:

A "computing device," "electronic device," or "computer" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, mobile electronic devices such as smartphones, Internet-connected wearables, tablet computers, laptop computers, and appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIG. 6.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

Figure 1:
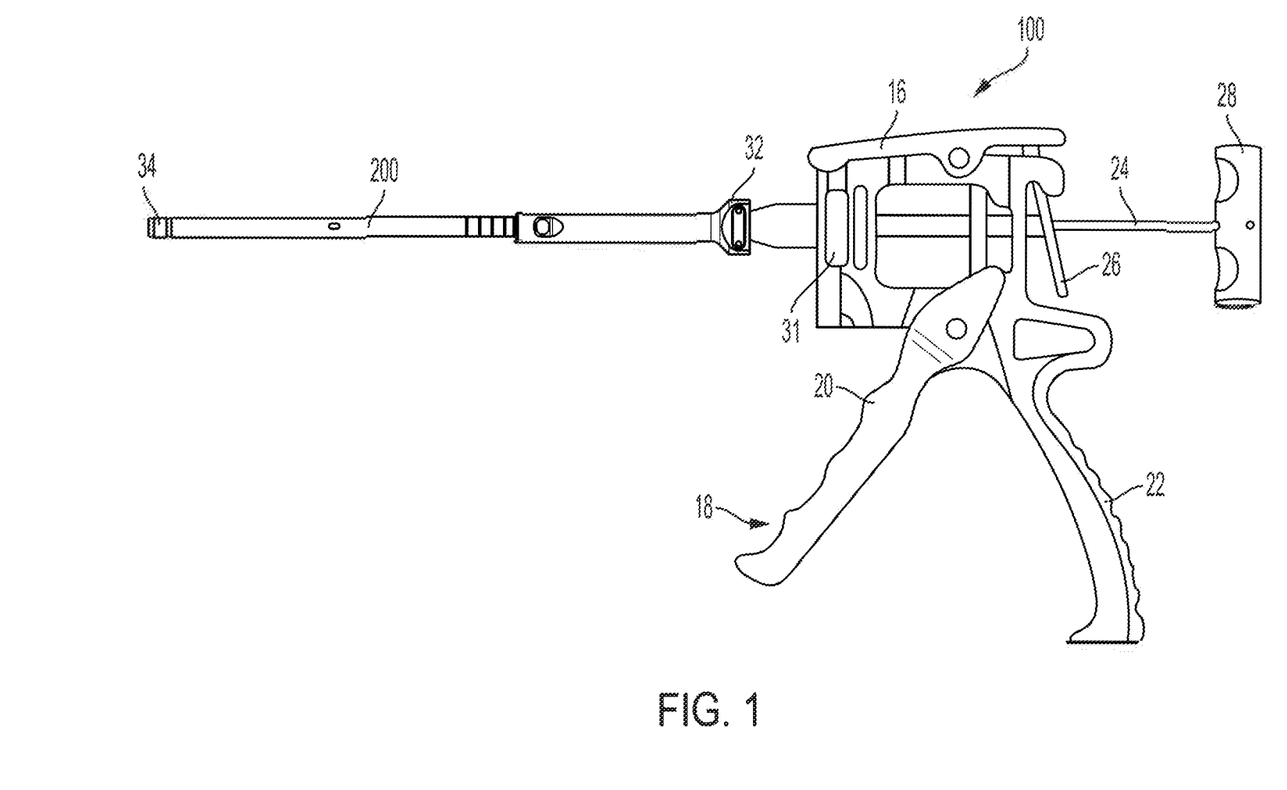
FIG. 1 illustrates an example graft delivery device.

The system(s) and method(s) described in this disclosure are generally directed to accurately dispensing bone graft material, e.g., during a procedure. FIG. 1 shows an example graft delivery device 100 according to an aspect of the disclosure. The device 100 includes a delivery tube 200 (described in more detail in FIGS. 2A and 2B), and an actuation mechanism 18. The actuation mechanism 18 is configured to apply a force to graft material disposed in the tube 200, causing the graft material to be dispensed through an open distal end 34 of the tube 200. The actuation mechanism 18 includes a receiving mechanism 31 configured to receive and lock (or otherwise secure) the proximal end 32 of the tube 200, so that the proximal end 32 of the tube 200 is adjacent to or abuts the actuation mechanism 18, allowing the actuation mechanism 18 to apply the force to the graft material. In the example device 100 of FIG. 1, the actuation mechanism 18 includes a frame 16 or similar structure which supports other components of the actuation mechanism 18, including components through which a user may actuate or otherwise manipulate the device 100. The example device 100 includes a first handle 20 and a second handle 22. The example actuation mechanism 18 of FIG. 1 is configured to apply the force to the graft material when the first handle 20 and second handle 22 are squeezed together. In some examples, the actuation mechanism 18 is coupled to a rod 24 and is configured to cause the rod 24 to advance toward the distal end 34 of the tube 200 when the actuation mechanism 18 is actuated. In some examples, a force is transmitted through the rod 24 to the graft material. For example, each time a user squeezes the handles (20,22) together, the actuation mechanism 18 may cause the rod 24 to advance by a fixed distance, where the rod 24 is either directly or indirectly in contact with the graft material. The actuation mechanism 18 may include a ratchet mechanism so that as the handles are alternately squeezed and released, the rod 24 advances toward the distal end 34 of the tube 200 in a series of steps. Other actuation mechanisms are also within the scope of this disclosure.

The actuation mechanism 18 of FIG. 1 also includes a release mechanism 26 configured to release the force applied to the graft material when the release mechanism 26 is pressed or otherwise manipulated. The force applied to the graft material may be further reduced by pulling on a handle 28 disposed at the end of the rod 24, causing the rod 24 to retreat from the distal end 34 of the tube 200. With the force released, additional graft material may be received through the open distal end 34 of the tube 200. After graft material is loaded into the tube 200, the open distal end 34 of the tube 200 may be disposed at a target site, such as a vertebra or other bone of a subject 102 (FIG. 4) undergoing a procedure. By squeezing the handles (20, 22) of the device 100 together, a user, such as a surgeon or other medical professional, may deliver a quantity of bone graft material to the target site. The systems and methods described in this disclosure are generally disclosed to accurately dispensing a volume of graft material even when the dispensed material is not directly observable (e.g., when the material is dispensed during a stereotactic or other robotically guided and/or minimally invasive percutaneous procedure, where the distal end 34 of the tube 200 has been inserted through a small incision in the skin of the subject 102 and is obscured from the surgeon's view).

Figure 2A:
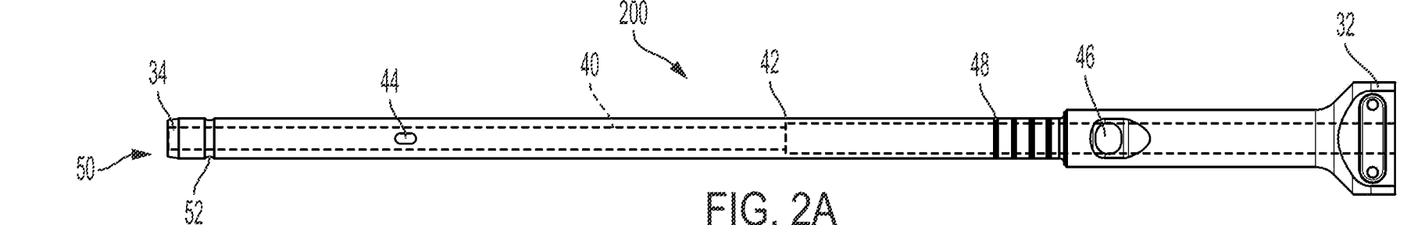
FIGS. 2A-2D illustrate a tube and plunger of the example graft delivery device.
Figure 2B:
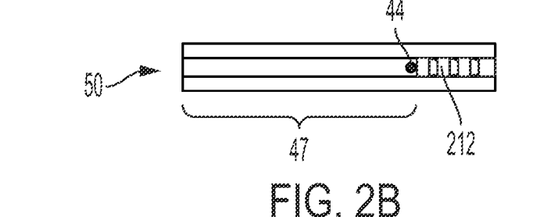

Referring to FIG. 2A, an enlarged view of the tube 200 is shown. The tube 200 defines a lumen 40 running longitudinally within tube 200 and configured to receive a plunger 210. The lumen 40 extends to the distal end 34 of the tube 200 to form a distal opening 50. The tube 200 includes a pressure relief opening 44 through the wall of the tube 200, forming a pressure chamber 47 (FIG. 2B) in the region of the lumen 40 between the open end 50 and the pressure relief opening 44. The pressure relief opening 44 may be sized to be small in comparison to the chamber so that pressure may be applied to graft material within the chamber 47, but gasses and/or other fluids (either compressible or non-compressible) may pass through the opening 44, leaving compressed graft material in the pressure chamber 47. In an example, lumen 40 has a diameter of approximately 6 mm and includes two pressure relief openings 44. In this example, each pressure relief opening 44 may be an oval shape, e.g., approximately 4 mm×2 mm, and the pressure relief openings 44 may pass through opposite side walls of the lumen 40. Other configurations of pressure relief openings 44 are also within the scope of this disclosure. The configuration (e.g., number, shape, and size) of the pressure relief opening(s) 44 may be varied to adjust the input force applied by the user to pressurize the chamber 47. An enlarged view of the portion of the tube 200 including the pressure chamber 47 is shown in FIG. 2B. The pressure chamber 47 may be sized to hold sufficient graft material for one or more applications. For example, the pressure chamber 47 may be sized to hold 2 cubic centimeters of graft material, which may be sufficient for two maximum size vertebra defects. Other volumes of pressure chambers 47 are also within the scope of this disclosure, including, but not limited to 1 cubic centimeter. The tube 200 also includes a dosage window 46 through which a portion of the plunger 210 is visible when the plunger 210 is disposed within the lumen 40 of the tube 200. The tube 200 may also include fiducial markings 48 along its length for use during robot-assisted surgery (described in more detail below and shown in FIG. 4). The tube 200 may also include ridges, notches, threads, or other structure in the outer wall of the tube 200, forming a retention member 52 allowing a graft loading device 306 (e.g., 306, FIG. 3C) to be secured to the tube 200.

Figure 2C:
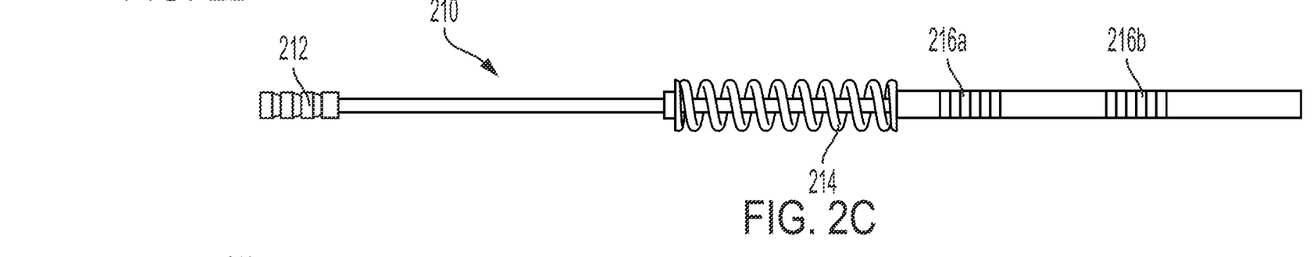
Figure 2D:
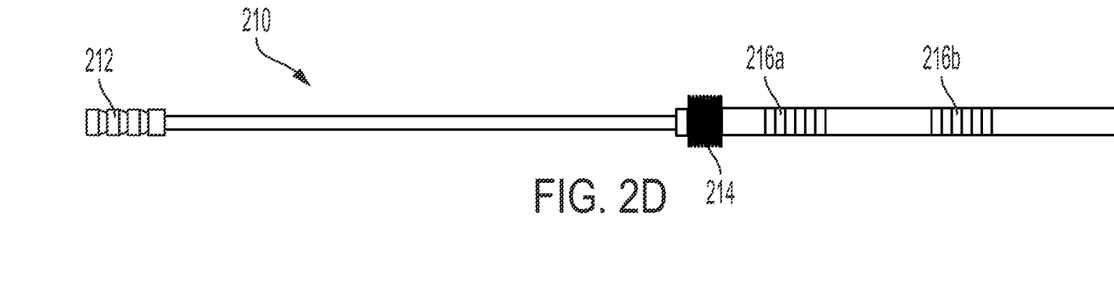

Referring to FIG. 2C, an example plunger 210 is shown. The plunger 210 may be formed of a material capable of transferring a force from the actuation mechanism 18 to the graft material, such as polyether ether ketone (PEEK) or stainless steel. At its distal end, the plunger 210 may include a piston 212 having a diameter consistent with the bore (e.g., diameter) of the lumen 40 in the region of the pressure chamber 47. The piston 212 may be configured to form a seal with the lumen 40, so that when graft material is disposed in the pressure chamber 47, and a force is applied to the plunger 210 in the direction of the distal end 34, the force is translated to the graft material. Furthermore, the seal between the piston 212 and the lumen 40 is configured to reduce or eliminate graft material escaping around the piston 212, increasing accuracy of the volume of graft material delivered. The piston 212 may be configured to form a seal with the pressure relief opening 44, preventing the escape of pressure from the pressure chamber 47 through the opening 44. In some examples, the piston 212 is formed of stainless steel (e.g., SAE Type 630 stainless steel). The piston 212 may include one or more ring grooves configured to further enhance sealing the piston 212 against the lumen 40. These ring grooves may be enhanced with piston rings to further improve the sealing quality of the piston 212. In some examples, the ring grooves do not include piston rings, but any graft material that leaks past the end of the piston 212 further improves the sealing quality of the piston 212 much like a piston ring would. That is, graft material that leaks past the distal tip of the piston 212 is caught in the first ring groove, forming a seal. Graft material that leaks from the first ring grove is caught in the second ring groove, forming a second seal, and so forth. The configuration (e.g., number and spacing) of the ring grooves may be configured based on characteristics of the graft material to adjust the input force applied by the user to pressurize the chamber 47. The plunger 210 may further include a spring member 214 configured to apply a force to the plunger 210 in a direction away from the distal end 34 of the tube 200 when the plunger 210 is disposed in the lumen 40. The lumen 40 may be configured for compatibility with the plunger 210. For example, the lumen 40 may have a non-uniform diameter. The example tube 200 shown in FIG. 2A includes a shoulder 42 formed by a step change in diameter between a larger diameter near the proximal end 32 and a narrower diameter near the distal end 34. The shoulder 42 may provide a surface against which one end of the spring member 214 may be disposed so that as the plunger 210 is further advanced toward the distal end 34, the spring member 214 is compressed, causing the spring member 214 to impart the force on the plunger 210. FIG. 2C shows the plunger 210 in an extended state, e.g., after graft material has been loaded into the pressure chamber 47. FIG. 2D shows the example plunger 210 with the spring member 214 in a compressed state, e.g., after graft material has been dispensed from the device 100. In this compressed state, the force applied by the spring member 214 may be opposed by the force applied by the actuation mechanism 18. Referring back to FIG. 1, the force applied by the actuation mechanism 18 may be released by release mechanism 26. When the force applied by the actuation mechanism 18 is released, the force applied by the spring member 214 may cause the plunger 210 to retreat away from the distal end 34, expanding the available volume of the pressure chamber 47, allowing additional graft material to be loaded. The spring 214 may cause the plunger 210 to quickly return to a starting position (e.g., adjacent to, but not fully overlapping with, the pressure relief opening 44), allowing for faster reloading of graft material.

The plunger 210 may also include one or more dose scales 216a, 216b disposed on the plunger 210 such that the dose scales 216 are visible through the dosage window 46 when the plunger 210 is disposed in the lumen 40 of the tube 200. Each dose scale 216 may include one or more fiducial marking indicated a corresponding volume of graft material.

For example, the horizontal distance between each fiducial marking may indicate a corresponding volume of 0.2 cubic centimeters of graft material (or other suitable increment of graft material volume). To further facilitate reading the dose scale 216, significant markings (e.g., one "full" dose, one "half" dose), may be configured to stand out from the others (e.g., by being darker or wider). A dose may be in the range from 0.1 to 10 cubic centimeters or other suitable range based on e.g., the procedure being performed.

As the plunger 210 advances toward the distal end 34, the user may observe, through the dosage window 46, the corresponding movement of the fiducial marking of the dose scale 216. That is, the dosage window 46 is configured to be in the line of sight of the user as the user actuates the graft delivery device 100. By actuating the actuation mechanism 18 while observing the movement of the dose scale 216 through the dosage window 46, the user may accurately dispense a volume of graft material to a target site, such as a bone of a subject 102 undergoing a procedure.

Figure 3A:
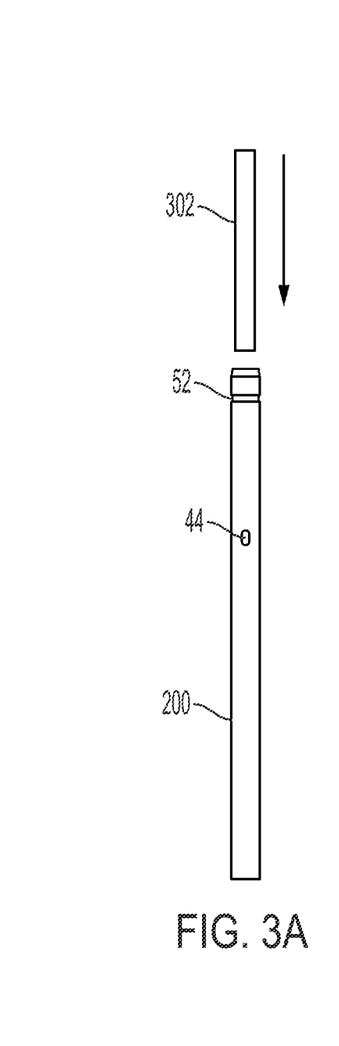
FIGS. 3A-3C illustrate methods of loading graft into the example graft delivery device.
Figure 3B:
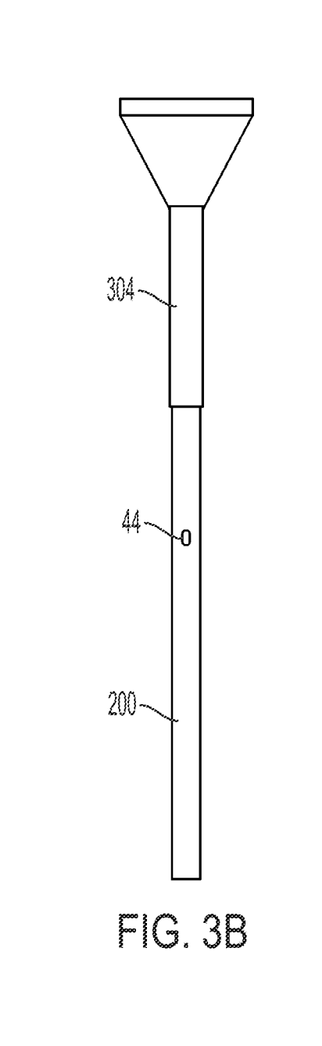
Figure 3C:
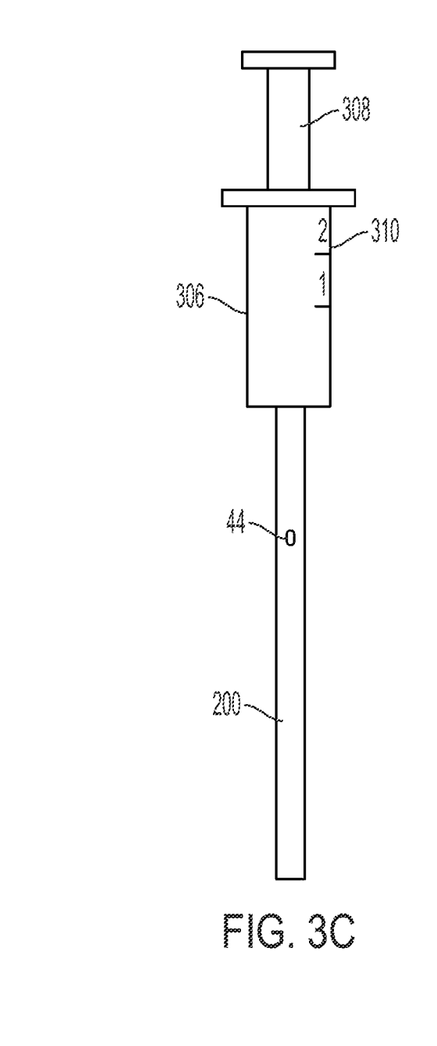

FIGS. 3A, 3B, and 3C, show methods of loading graft into the example graft delivery device 100. As shown in FIG. 3A, the graft material is first loaded into a container such as a cartridge 302 before being loaded into the pressure chamber 47 of the tube 200. The cartridge 302 may be configured (e.g., sized) to easily, but snugly, fit though the open end 50 of the tube 200. In one example, the cartridge 302 includes a split tube into which the graft material may be loaded and formed into a substantially cylindrical shape. In this example, cartridges 302 may be pre-loaded with graft material, e.g., prior to a surgical procedure. After the graft material is loaded into the pressure chamber 47, the user may tamp down the graft material, e.g., by pressing with a rod or similar device (not shown) until graft material issues from the pressure relief opening 44. As the user continues to press the graft material into the pressure chamber 47, voids that may be present in the material are removed. The pressure relief opening 44 allows voids to be removed even when the rod is tight-fitting and would not allow, e.g., gasses or other fluids that make up the voids to escape through the open end 50. By removing voids in the loaded graft material, the material may then be more accurately dispensed or meted out. That is, the remaining material more fully occupies the available volume of the lumen 40. Therefore, translation of the plunger 210 by a measured distance toward the open end 50 more accurately corresponds to a volume of graft material dispensed. Accordingly, longitudinal movement of the dose scale 216 (visible through the dosage window 46) more accurately corresponds to a volume of graft material. The pressure relief opening 44 (e.g., orifice) may be sized to allow the user to efficient remove voids in the graft material without excess loss of graft material through the opening 44.

As shown in FIG. 3B, the graft material may also be guided into the open end 50 of the tube 200 using a funnel 304 or similar device. After the graft material is loaded through the funnel 304 into the pressure chamber 47, the graft material may be compressed to remove voids as described above. FIG. 3C shows an example graft loading device 306. The user may secure the graft loading device 306 to the retention member 52 (described above) after loading graft material into the graft loading device 306. In some examples, the graft loading device 306 screws into, clamps onto or otherwise engages with or mates with the retention member 52. In some examples, the graft loading device 306 includes a standard syringe adapted to mate with the retention member 52, e.g., via a syringe adapter. The syringe may screw into or otherwise mate with the syringe adapter. The adapter may include a spring detent mechanism configured to "snap" into and out of a groove (e.g., retention member 52) on the distal end of the tube 200, e.g., when a button is depressed on the syringe adapter. When the button of the syringe adapter is released (not depressed) the spring detent of the syringe adapter may be locked to the retention mechanism 52, and may be unable to "snap" out of the groove. After the graft loading device 306 is secured in place, graft material may be loaded (e.g., transferred) from the graft loading device 306 to the pressure chamber 47 of the tube 200. After loading is complete, the graft loading device 306 may be unlocked and removed from the tube 200. Because the graft loading device 306 is quickly and easily locked and unlocked, the graft delivery device 100 is quickly and easily reconfigured between loading and delivery modes. Similar to the other graft loading methods, the loaded graft material may be compressed to remove voids in the graft material. In this example, the user may operate the graft loading device 306 (e.g., by pushing on a plunger 308, similar to the plunger of a syringe or other operating or actuator mechanism) to apply pressure to the loaded graft material. In some examples, the graft loading device 306 is operated by a bellows or other mechanism suitable for applying pressure to the graft material. The graft loading device 306 may be operated manually or may be powered. Because the graft loading device 306 is securely attached to the tube 200, the graft material may be transferred to the pressure chamber 47 of the tube 200 and compacted within the pressure chamber 47 through the action of the plunger 308. The graft loading device 306 may also be pre-loaded with graft material, e.g., prior to a surgical procedure. Furthermore, the graft loading device 306 may be configured to hold a specific volume of graft material, or may include a graduated scale 310 or other markings indicating a volume of graft material contained in the graft loading device 306 prior to, during, and subsequent to transfer to the pressure chamber 47.

Figure 4:
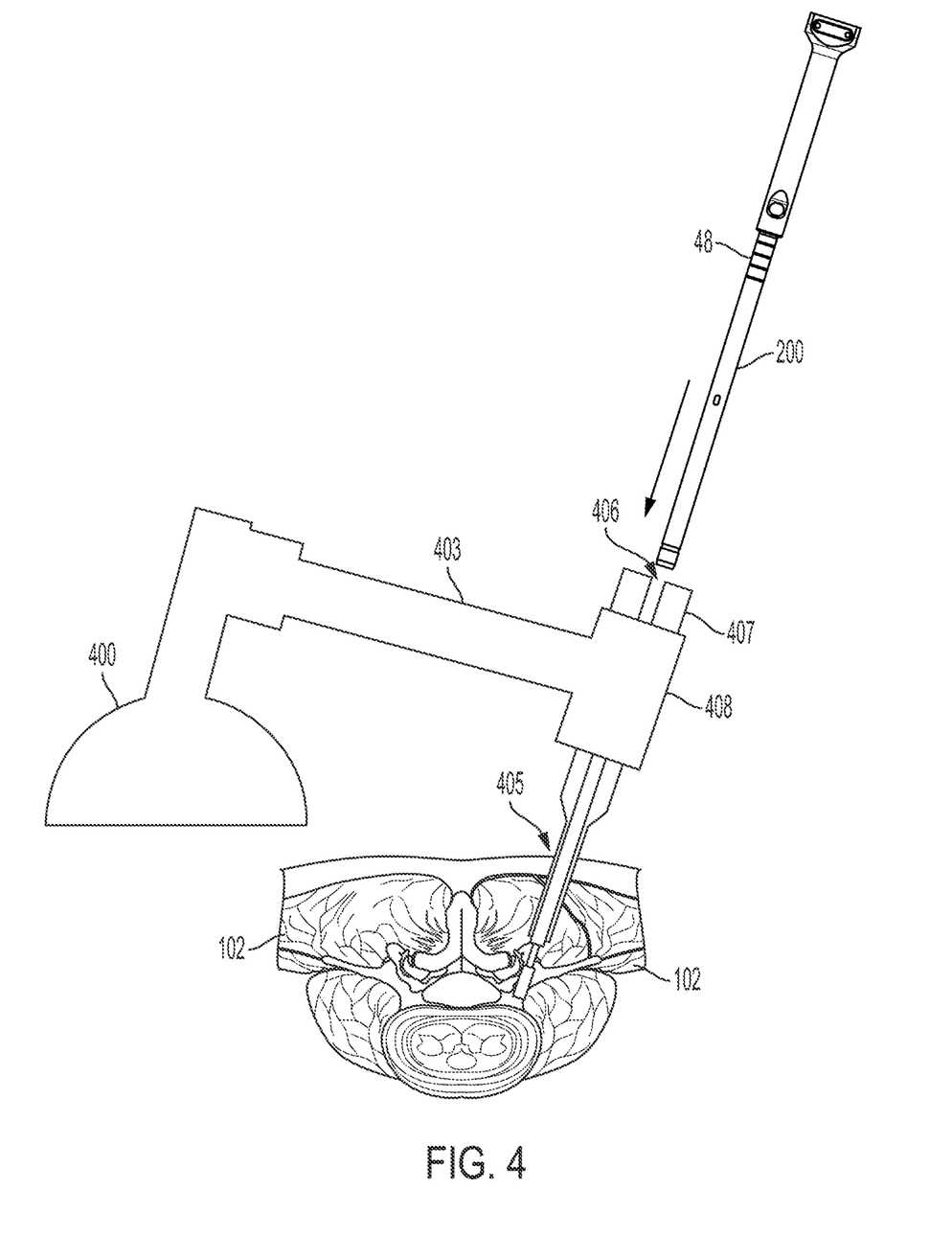
FIG. 4 illustrates robot-assisted surgery using the example graft delivery device.

FIG. 4 shows an example of the graft delivery device 100 used in robotic-assisted surgery. In this example, a robotic system 400 assists placement of surgical tools. The robotic system 400 may be rigidly mounted to a surface such as a floor or table of an operating room. Here, the robotic system 400 includes a robot arm 403 supporting a guide sleeve 408 and has multiple joints configured to rotate and/or articulate, providing the arm 403 with multiple degrees of freedom. The guide sleeve 408 may be positioned and oriented by manipulating joints of the robotic system 400. The guide sleeve 408 may be used to guide or position surgical tools and/or the graft delivery device 100, by establishing a position, orientation, and a trajectory for instruments to follow as the instruments are inserted into the guide sleeve. The trajectory may include an incision point, e.g., in the fascia of the subject, through which the distal end of one or more instruments may pass. In some examples, the tube 200 of the graft delivery device 100 is sufficiently rigid for the distal end 34 to be to be accurately positioned by the robotic system 400 (e.g., when the tube 200 of the graft delivery device 100 is fully inserted in the guide sleeve 408 of the robotic system 400). The robotic system 400 may be controlled by a computing device, e.g., including equipment or components shown in FIG. 6. The computing device may include or have access to a data store containing medical records and/or medical images, such as x-rays, or the result of a Computed Tomography (CT) scan, or the like. The computing device may also interface with the robotic system 400 through a wired or wireless communication channel, such as a computer communication network, and may be configured to transmit commands or signals through the communication channel to control movement of the robotic system 400. In some examples, the computing device is configured to execute surgical planning and execution software. The surgical planning and execution software may include a surgical plan associated with the subject 102. The surgical plan may be developed prior to surgery and may be based on medical images, medical records, surgeon preferences, available surgical implants, prior outcomes or other subjects, and so forth. In some examples, the plan may target a facet of a vertebra. The plan may include creating a void in the facet (e.g., using a burr), then precisely filling the void based on the depth and diameter of the created void. In another example, the plan may target the space between or alongside one or more vertebrae, e.g., over the transverse processes, such as during a posterolateral fusion procedure. In some examples, the plan may target more than one graft delivery site through the same incision point. In each of these cases, the plan may include a predetermined volume of graft to accurately dispense at each delivery site using the graft delivery device 100.

In some examples, the computer-based surgical planning and execution system is configured to control the joints of the robotic system 400, e.g., operating the joints to position and orient the sleeve 408 according to a defined surgical plan for the subject 102. The surgical planning and execution system may develop the surgical plan based on medical record information related to the subject 102 and/or medical images, such as x-ray, CT scan, or magnetic resonance imaging (MM) scans of the subject 102 taken prior to the surgery. In some examples, the surgical planning and execution system applies a trained machine-learning model to the medical record information and/or medical images to determine the surgical plan prior to surgery. The surgical plan may include a model post-operative anatomical configuration of the subject 102 based on the medical record information and/or medical images and based on surgical outcomes of other patients (e.g., post-operative medical record information and/or medical images of other patients). The surgical planning and execution system may also be configured to receive sensor data during the surgical procedure from sensors attached to the subject 102 which measure or track the position and orientation of anatomical structures (such as the position and orientation of one or more vertebrae) of the subject 102, and/or the position of one or more surgical tools, and adjust the surgical plan in real-time based on the sensor data.

As shown in FIG. 4, the robotic system 400 may position and orient the guide sleeve 408 with respect to a surgical site 405 of the subject 102. The surgical site 405 is the general area of the subject 102 where the surgery takes place. In some examples, the surgical site 405 include a point of incision through the skin or facia of the subject 102 through which surgical tools and/or implants may pass. In the case of minimally invasive surgery (e.g., percutaneous surgery), the incision may be as small as reasonably possible. Furthermore, the point of incision may be located to avoid undue harm to the subject 102. For example, the point of incision may be located at a threshold distance away from sensitive tissue or anatomical areas. In some cases, the point of incision may be located to minimize the amount of tissue a surgical tool must pass through during the surgery. In some examples, a cannula 407 is disposed in the sleeve 408. The cannula 407 may be tightly mated (e.g., with a clearance or interference fit) with the sleeve 408, preventing transverse movement of the cannula 407 within the sleeve 408. Furthermore, the cannula 407 may include a flange or collar near its proximal end, such that the cannula 407 may be inserted in the sleeve 408 until the flange/collar contacts the proximal end of the sleeve 408, thus preventing further longitudinal movement of the cannula 407. In other embodiments, the cannula 407 lacks a collar and is fully inserted within the sleeve 408. In these embodiments, further longitudinal movement of the cannula 407 is prevented by the friction fit between the cannula 407 and the sleeve 408. The cannula 407 may include a distal portion which protrudes beyond the sleeve 408. The distal portion may extend through the incision of the subject 102 to a point within the body of the subject 102, e.g., to help reduce the chance of infection or other harm to the subject 102.

The cannula 407 may include a hollow central tube 406 through which, e.g., surgical tools may pass. The surgical tools may be inserted from the proximal end of the cannula 407 and pass through the cannula 407 and the incision into the body of the subject 102. In some examples (e.g., as shown in FIG. 4), the tube 200 of the graft delivery device 100 is inserted into the cannula 407. The tube 200 may include a flange, rib, stop or may be otherwise configured to limit the distance that the tube 200 can be inserted into the cannula 407. The robotic system 400 may have positioned the guide sleeve 408 so that when the tube 200 is fully inserted in the cannula 407 (up to the flange/stop), the distal end 34 is accurately positioned at the target site. After the graft delivery device is positioned, the user may dispense the graft material by actuating the actuation mechanism 18 while observing the dose scale 216 through the dosage window 46. As shown in FIG. 4, a portion of the tube 200 near the proximal end 32 has a sufficiently large diameter (e.g., larger than the distal portion of the tube 200) that the proximal portion of the tube serves as a stop, limiting the distance the tube 200 may be inserted into the cannula 407. The dosage window 46, disposed in the proximal portion, remains visible when the tube 200 is fully inserted within the cannula 407.

The tube 200 may include fiducial markings 48 along its length. In some examples, the fiducial marking 48 indicates a distance from a fully inserted configuration. The example tube 200 of FIG. 4 shows four marking, although more or fewer markings are within the scope of this disclosure. As shown in FIG. 4, when the tube 200 is fully inserted in the cannula 407, none of the fiducial markings 48 are visible. As the tube 200 is withdrawn from the cannula 407, more and more fiducial markings 48 become visible. The fiducial markings 48 may be used for a variety of purposes. For example, as graft is dispensed at the target site, the force of the graft at the site may push the graft delivery device 100 away from the site (e.g., longitudinally back though the cannula 407 or guide sleeve 408). The number of visible fiducial markings 48 may indicate how far (in units of distance) the device 100 has been pushed away from the target site. The fiducial markings 48 may also (or alternatively) indicate an equivalent amount of excess graft material that was applied at the target site, causing the tube 200 to be pushed back.

Figure 5:
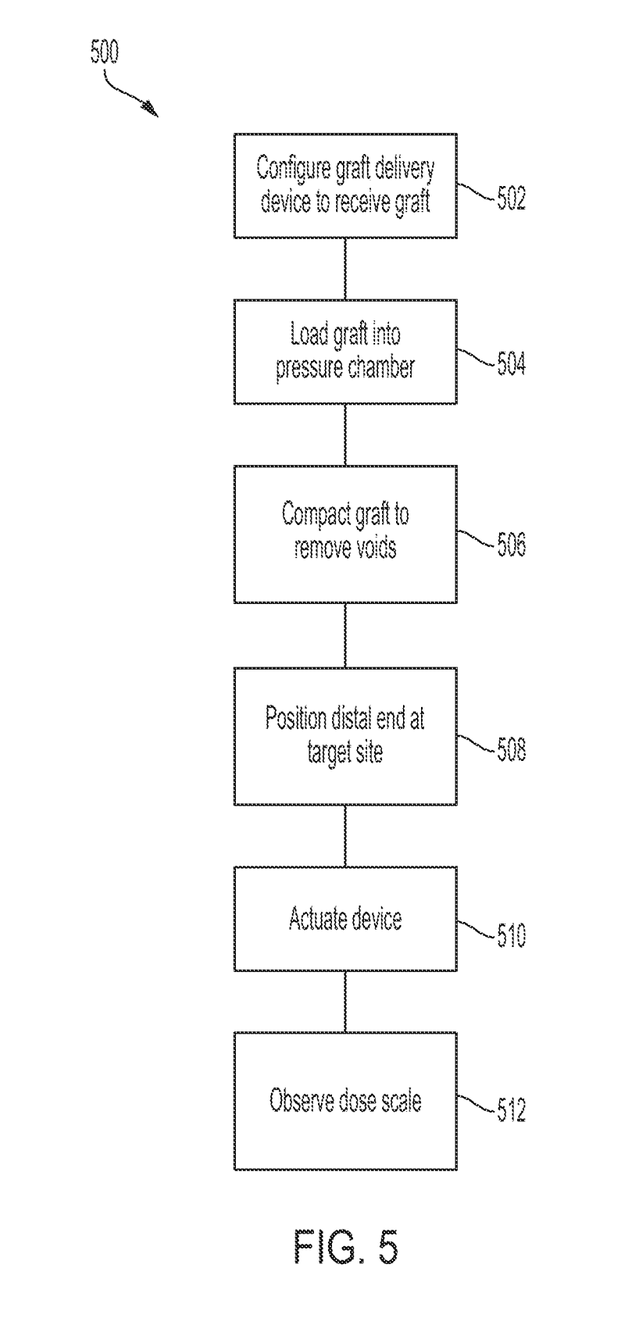
FIG. 5 is a flowchart of a method for delivering graft material.

FIG. 5 is a flowchart of a method 500 for delivering graft material to a target site, e.g., during a procedure performed on a subject 102. At step 502, the method 500 includes configuring the graft delivery device 100 to receive graft material. In some examples, configuring the graft delivery device 100 to receive graft material includes positioning the piston 212 of the plunger 210 adjacent to (but not fully covering) the pressure relief opening 44, such that the distal end of the piston 212 defines a wall of the pressure chamber 47 (see, e.g., FIG. 2B) leaving the pressure relief opening 44 exposed. Using the example graft delivery device 100 of FIGS. 1, the plunger 210 may be advanced toward the distal end 34 using the actuation mechanism 18, and the plunger 210 may be withdrawn away from the distal end 34 using the release mechanism 26 and/or the handle 28. The plunger 210 can thereby be moved forward and backward within the lumen 40 to the desired position. Furthermore, the dose scale 216 may include a "home" fiducial marking to indicate when the piston 212 is positioned adjacent to the pressure relief opening 44 (e.g., at a "home" or starting position).

At step 504, the method 500 includes loading graft material into the pressure chamber 47 of the tube 200. Graft material may be loaded into the device using any of the techniques shows in FIGS. 3A-3C and described above. After graft material has been loaded into the pressure chamber 47, the method 500 includes (at step 506) compacting the graft material to remove voids. The graft may be compacted using the techniques described above.

At step 508, the method 500 includes positioning the distal end 34 of the graft delivery device 100 at the target site. In some examples, positioning the distal end 34 of the graft delivery device 100 at the target site includes fully inserting the graft delivery device 100 in a guide sleeve (or cannula) of a robotic system 400. In other examples, the user manually positions the distal end 34 of the graft delivery device 100.

At step 510, the method 500 includes actuating the graft delivery device 100. Actuation mechanisms include handles 20, 22 which move with respect to each other, levers, electric or hydraulic motors, etc. In some examples, actuating the graft delivery device 100 causes a plunger 210 disposed with the lumen 40 to advance toward the distal end 34, displacing graft material as it advances.

At step 512, the method 500 includes observing the dose scale 216 through the dosage window 46. As described above, the dose scale 216 accurately indicates a volume of compacted graft material dispensed from the graft delivery device 100. In some examples, the computer-based surgical planning and execution system indicates an expected volume of graft material to dispense, based on the surgical plan for the subject 102. When the graft delivery device 100 is disposed in a holder, such as the guide sleeve 408 of a robotic system 400, the user may also observe fiducial marking 48 along the length of the tube 200 of the graft delivery device 100, which indicate if, and how far, the graft delivery device 100 has been pushed backwards in the holder while graft material is dispensed (e.g., along the trajectory defined by the axis of the guide sleeve 408.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 6:
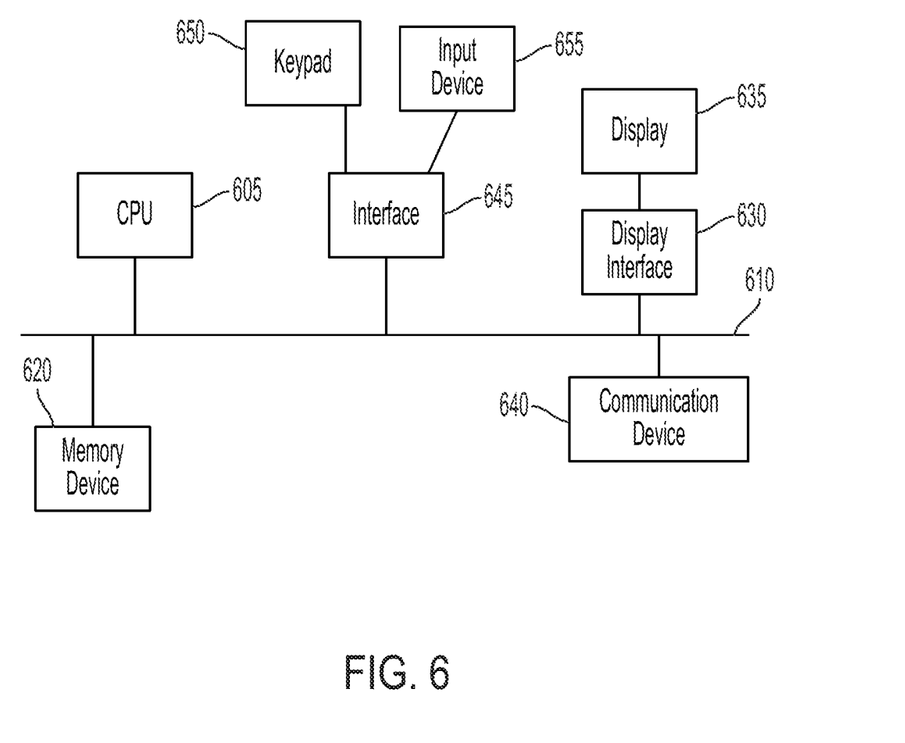
FIG. 6 shows a block diagram of an example of internal hardware that may be used to contain or implement program instructions according to an embodiment.

FIG. 6 illustrates example hardware that may be used to contain or implement program instructions. A bus 610 serves as the main information highway interconnecting the other illustrated components of the hardware. Central Processing Unit (CPU) 605 is the central processing unit of the system, performing calculations and logic operations required to execute a program. CPU 605, alone or in conjunction with one or more of the other elements disclosed in FIG. 6, is an example of a processor as such term is used within this disclosure. Read only memory (ROM) and random-access memory (RAM) constitute examples of non-transitory computer-readable storage media 620, memory devices or data stores as such terms are used within this disclosure.

Program instructions, software or interactive modules for providing the interface and performing any querying or analysis associated with one or more data sets may be stored in the memory device 620. Optionally, the program instructions may be stored on a tangible, non-transitory computer-readable medium such as a compact disk, a digital disk, flash memory, a memory card, a universal serial bus (USB) drive, an optical disc storage medium and/or other recording medium.

An optional display interface 630 may permit information from the bus 610 to be displayed on the display 635 in audio, visual, graphic or alphanumeric format. Communication with external devices may occur using various communication ports 640. A communication port 640 may be attached to a communications network, such as the Internet or an intranet.

The hardware may also include an interface 645 which allows for receipt of data from input devices such as a keypad 650 or other input device 655 such as a touch screen, a remote control, a pointing device, a video input device and/or an audio input device.

It will be appreciated that the various above-disclosed and other features and functions, or alternatives thereof, may be desirably combined into many other different systems or applications or combinations of systems and applications. Also, that various presently unforeseen or unanticipated alternatives, modifications, variations or improvements therein may be subsequently made by those skilled in the art which are also intended to be encompassed by the following claims.

What is claimed is:

1. A device for delivering graft material to a target site, the device comprising:
   an actuation mechanism;
   a tube defining a lumen and an open end, the tube configured to receive graft material through the open end, wherein the tube comprises:
      a pressure relief opening disposed in a wall of the tube, the pressure relief opening defining a pressure chamber between the open end and the pressure relief opening; and
      a dosage window;
   a plunger positioned within the lumen of the tube and coupled to the actuation mechanism such that at least a portion of the plunger or the actuation mechanism is visible through the dosage window, wherein the actuation mechanism is configured to advance the plunger toward the open end to deliver graft material through the open end; and wherein the plunger comprises a spring configured to provide a longitudinal force to the plunger in a direction away from the open end.

2. The device of claim 1, wherein the pressure relief opening is configured to allow fluid to escape the lumen as graft material is received through the open end into the pressure chamber.

3. The device of claim 1, wherein the portion of the plunger or the actuation mechanism that is visible through the dosage window comprises a dose scale indicating an associated volume of graft material.

4. The device of claim 1, wherein a volume of the lumen between the open end and the pressure relief opening is at least 2 cubic centimeters.

5. The device of claim 1, wherein the tube is configured to engage with a guide sleeve of a robot arm.

6. The device of claim 1, wherein the tube comprises one or more fiducial markings along its length, the one or more fiducial markings indicating a distance.

7. The device of claim 1, wherein the plunger comprises a distal end which forms a seal with the lumen.

8. The device of claim 7, wherein the distal end comprises a series of ring grooves.

9. The device of claim 1, wherein the plunger is formed of polyether ether ketone.

10. The device of claim 1, wherein the actuation mechanism includes a ratchet mechanism.

11. The device of claim 1, wherein the tube comprises a retention member disposed near the open end and configured to retain a graft loading device.

12. The device of claim 11, wherein the graft loading device comprises:
a graduated scale indicating a volume of graft material contained in the graft loading device; and
an actuator configured to transfer graft material from the graft loading device to the device and to compact the graft material in the pressure chamber.

13. A system comprising:
a device for delivering graft material to a target site, the device comprising:
an actuation mechanism;
a tube defining a lumen and an open end, the tube configured to receive graft material through the open end, wherein the tube comprises:
a pressure relief opening disposed in a wall of the tube, the pressure relief opening defining a pressure chamber between the open end and the pressure relief opening; and
a dosage window; and
a plunger positioned within the lumen of the tube and coupled to the actuation mechanism such that at least a portion of the plunger or the actuation mechanism is visible through the dosage window, wherein the actuation mechanism is configured to advance the plunger toward the open end to deliver graft material through the open end; and
a robotic system comprising a robot arm, wherein the robot arm comprises a guide sleeve configured to receive the tube of the device, the robotic system configured to position and orient the guide sleeve such that a distal end of the device, when fully inserted in the guide sleeve, is positioned at a target site according to a surgical plan;
wherein the plunger comprises a spring configured to provide a longitudinal force to the plunger in a direction away from the open end.

14. A system comprising:
a device for delivering a graft material to a target site, the device comprising:
a tube defining a lumen and an open end, the tube configured to receive graft material through the open end, wherein the tube comprises:
a pressure relief opening disposed in a wall of the tube, the pressure relief opening defining a pressure chamber between the open end and the pressure relief opening; and
a retention member disposed near the open end and configured to retain a graft loading device;
a plunger positioned within the lumen of the tube; and
an actuation mechanism configured to advance the plunger toward the open end to deliver graft material through the open end; and
a graft loading device configured to engage the retention member of the tube, the graft loading device comprising:
a graduated scale indicating a volume of graft material contained in the graft loading device; and
an actuator configured to transfer the graft material from the graft loading device to the device and to compact the graft material in the pressure chamber;
wherein the plunger comprises a spring configured to provide a longitudinal force to the plunger in a direction away from the open end.

* * * * *